United States Patent [19]

Robinson

[11] Patent Number: 4,752,458
[45] Date of Patent: Jun. 21, 1988

[54] STRUCTURED SILICAS

[76] Inventor: Eric Robinson, 146 Moss Rd., Lisburn, Lambeg County, Ireland, BT27 4LF

[21] Appl. No.: 27,026

[22] PCT Filed: Jun. 5, 1986

[86] PCT No.: PCT/GB86/00319
  § 371 Date: Feb. 11, 1987
  § 102(e) Date: Feb. 11, 1987

[87] PCT Pub. No.: WO86/07345
  PCT Pub. Date: Dec. 18, 1986

[30] Foreign Application Priority Data

Jun. 12, 1985 [GB] United Kingdom ............... 8514815

[51] Int. Cl.$^4$ ............................................. C01B 33/12

[52] U.S. Cl. .................................... 423/335; 423/338; 423/339

[58] Field of Search ................. 423/338, 339, 335

[56] References Cited

U.S. PATENT DOCUMENTS 4,564,556 1/1986 Lange .................................. 428/325
4,621,936 11/1986 Hansson ............................. 401/215

Primary Examiner—John Doll
Assistant Examiner—Lori S. Freeman

[57] ABSTRACT

A method of preparing spherical microparticles of silica comprising adding an acid solution to a silicate solution before or after addition of an alkali metal alginate, ammonium alginate, starch, gelatin, pectin or mixtures thereof. The microparticles can be used to prepare macroporous materials having a controlled pore structure.

10 Claims, No Drawings

STRUCTURED SILICAS

This invention concerns the preparation of microspherical silica particles which can be formed into porous solids within which the interstitial pore structure can be controlled. Such materials are of value as supports for catalysts and biocatalysts, as chromatographic packing, as adsorbents and as supports for polymers used as chromatographic packing, adsorbents or ion exchange media.

Porous silica microspheres have been made by spray drying sols containing colloidal silica as disclosed in U.S. Pat. No. 3,301,635 and in U.S. Pat. No. 4,131,542. In another process for the production of microspheres in the 0.5 to 20 micron range disclosed in U.S. Pat. No. 4,010,242 colloidal silica particles are formed into microspheres by coacervation of urea or melamine formaldehyde resins which must be burned out later. The processes of the prior art do not provide silica microspheres which can be prepared in solution over a broad range of particle sizes by alteration of the process conditions and which can be formed into larger solid masses containing a controlled macropore structure.

The present invention provides a method of preparing microparticles of silica comprising adding an acid solution to a solution of a soluble silicate, and also adding an organic polymer solution comprising an alkali metal alginate, ammonium alginate, starch, gelatin, pectin or a mixture thereof.

The acid solution may be added to the silicate solution before or after addition of the polymer, that is to say the alkali metal alginate, ammonium alginate, starch, gelatin, pectin or mixtures thereof.

The microparticles produced by the invention may be substantially spherical having diameters of from 0.5 to 250 microns. The microparticles can be used to produce macroporous materials preferably having controlled pore structures.

Any soluble silicate such as sodium, potassium or ammonium silicate may be used and the solution should contain between 3% and 25% $SiO_2$ and preferably from 10% to 20% w/v $SiO_2$. The concentration of the polymer solution containing a soluble alginate, starch, gelatin, pectin or mixtures thereof should be between 0.1% and 25% w/v and preferably between 0.5% and 10% w/v. Any suitable acid may be used such as sulphuric, hydrocloric, nitric, acetic or phosphoric acid and the solution should contain from 1% to 10% by volume of the acid selected.

According to a preferred embodiment of the present invention an acid solution is added with stirring to a solution of a soluble silicate such that the pH remains above a value of 7. To this is added a solution containing a soluble alginate, starch, gelatin, pectin or mixtures thereof whereafter stirring may be discontinued and the mixture allowed to stand for between 1 and 24 hours. Each of the solutions is adjusted to and the mixture held at a constant temperature of between 0° and 100° C. The silica microspheres which form are separated from the liquor supernatent thereto, preferably by filtration, and are washed thoroughly using first hot and then cold water until largely free of organic matter followed by a dilute acid solution until largely free of any alkali metal ion present, and finally with cold water. The supernatent liquor may be recovered to allow extraction and reuse of the organic polymer. The filter cake may be masticated to break up any microsphere aggregates. If desired the microspheres may be dried at this stage by heating for example at 100° C. Alternatively the microspheres may be consolidated into a solid by for example pressing the filter cake. Consolidation is improved if after washing the microspheres are suspended in water and flocculated with polyethylene oxide for example using between 0.1% and 1.0% by weight of polyethylene oxide on the weight of silica. The macroporous solid formed is dried for example by heating at between 30° and 60° C. in a current of air. During drying little shrinkage occurs.

Before drying the filter cake may be shaped and will retain this shape after drying. Thus the moist microspheres may be formed into beads, tablets, pellets, or columns or may be extruded in a variety of shapes which will be retained on drying.

In the normal course of events the addition of an acid solution to a solution of a soluble silicate will within a period of time cause the formation of a continuous gel. In the present invention the time interval allowed between the addition of the acid solution to the solution of soluble silicate and the addition of the polymer solution should be such that gel formation has not taken place. It is not satisfactory to add the polymer solution after the typical gel structure has been allowed to form. The polymer solution may be added to the solution of soluble silicate. In this case the solution of acid may be added at any time. However in these circumstances the silica particles formed may not be as uniformly spherical in shape. Continuation of stirring after all the solutions have been thoroughly mixed can also lead to the formation of irregularly shaped particles.

The size of the silica microspheres produced according to the invention depends upon the concentrations of the solutions employed and the temperaure at which the solutions are mixed and held. Generally an increase in the concentration of the acid solution or a decrease in the concentration of the soluble silicate solution will each tend to cause an increase in the variability in the size of the microspheres produced and in the diameter of the larger particles formed. An increase in the concentration of the polymer solution tends to increase the microsphere size up to a limiting value beyond which no further increase is observed.

The pore size distribution and the pore volume of the macroporous solids produced from silica microspheres according to the invention depend upon the microsphere size used and upon the pressure applied to the undried consolidated material. Macroporous solids prepared according to the invention may have pore volumes ranging from 0.40 ml/ml to 0.88 ml/ml with surface areas of between 50 and 200 $m^2/g$. In the event that the size distribution of microspheres obtained is broader than is required to provide the desired pore structure the microspheres may be classified according to size. For microspheres laerger than 30 microns this is conveniently done by sieving. Smaller microspheres may be sized using a sedimentation cylinder.

The macroporous solids may additionally comprise other materials. Thus for example if it is desired to increase the pore volume further, powdered calcium carbonate may be mixed with the microspheres before consolidation. After drying this may be removed by treatment in an acid solution leaving voids in the structure. Alternatively, finely powdered ferromagnetic materials may be included in the structure to allow ready separation of the materials in use.

The strength of the macroporous silicas prepared may be increased by sintering at temperatures above 700° C. or by treatment with superheated steam at temperatures in excess of 120° C.

Macroporous beads made up of silica microspheres may be made directly by preparing the aforementioned mixture of a soluble silicate, an acid and a solution of a soluble alginate and dripping this mixture into a solution containing multivalent cations when the droplets form a gel bead by ionotropic gelatin. Alternatively an acid solution may be used in place of that containing multivalent cations. The beads are left in contact with the solution in which they are formed for at least 1 hour after which they are removed preferably by filtration and washed thoroughly until largely free of alkali metal ion. The beads may be dried by for example heating at 60° C. The organic material may be removed from these beads by heating at temperatures in excess of 500° C. leaving a macroporous bead of silica.

Macroporous silicas prepared according to the invention have particular application in the separation and immobilisation of large organic molecules for example protein molecules such as enzymes. Enzymes may be attached to the silica surface by adsorption or by covalent attachment or may be entrapped within a porous gel held in the macropores.

The invention will be further apparent from the following examples.

EXAMPLE 1

A commercial sodium silicate ($SiO_2:Na_2O$ ratio 3.2:1) was diluted with water until the $SiO_2$ content was 15% by weight. 100 ml 2% v/v sulphuric acid was added with stirring to 100 ml of the diluted sodium silicate followed by 50 ml of 4% w/v sodium alginate solution. After standing for six hours at 15° C. the solution was filled with a mass of silica microspheres which could be readily separated by filtration and were washed thoroughly with hot water, cold water, dilute sulphuric acid and finally cold water. The filter cake was pressed into a coherent mass at approximately $12 \times 10^4$ Pa and dried at 30° C. After drying the crushing strength was observed to increase with time. The final product had a Pore Volume of 0.88 ml/ml and a Density of 0.42 g/ml.

EXAMPLE 2

100 ml of 2% sulphuric acid was added with stirring to 100 ml of a 50% solution of commercial sodium silicate ($SiO_2:Na_2O$; 3.2:1) followed by 50 ml of 4% sodium alginate solution. After 6 h at 15° C. the resulting silica microspheres were washed by decantation ten times with 1000 ml aliquots of water. To the final wash 5 ml of 1% polyethylene oxide (M.W. 5,000,000) was added. The silica was separated by filtration and squeezed to consolidate then air dried.

Examination under the electron microscope at magnification 2000× showed that the solid was made up of porous spherical particles between 1 and 30 microns in diameter bonded together at points of contact and having large interstices interconnecting throughout the structure. The Pore Volume was 0.62 ml/ml and the Density 0.60 g/ml.

EXAMPLE 3

A series of samples were prepared as in Example 1 but with the temperature of the solutions and of the mixture selected to demonstrate the effect of temperature on the product.

| Temperature °C. | Microsphere Size microns | Pore Volume ml/ml | Weight Porosity ml/g | Density g/ml |
| --- | --- | --- | --- | --- |
| 30 | 2–30 | 0.60 | 0.95 | 0.60 |
| 40 | 4–6 | 0.66 | 1.15 | 0.58 |
| 60 | 3–4 | 0.70 | 1.26 | 0.56 |
| 80 | 1–2 | 0.71 | 1.35 | 0.53 |
| 100 | 0.5–2 | 0.71 | 1.36 | 0.52 |

EXAMPLE 4

A series of samples were prepared as in Example 1 but with the temperature held constant at 18° C., the acid concentration 1.75% v/v and the concentration of the sodium alginate solution varied to demonstrate the effect on the product.

| Alginate Concn. % w/v | Microsphere Size microns | Pore Volume ml/ml | Weight Porosity ml/g | Density g/ml |
| --- | --- | --- | --- | --- |
| 0.1 | 0.5–1 | 0.58 | 0.85 | 0.68 |
| 0.5 | 1–2 | 0.70 | 1.04 | 0.68 |
| 1.0 | 3–5 | 0.77 | 1.47 | 0.52 |
| 4.0 | 5–10 | 0.83 | 3.74 | 0.22 |
| 8.0 | 5–7 | 0.79 | 2.24 | 0.35 |

EXAMPLE 5

Two samples were prepared as in Example 1 using a 2% solution of sodium alginate and the filter cake was pressed at two pressures to demonstrate the effect on the product.

| Pressure Pa | Pore Volume ml/ml | Weight Porosity ml/g | Density g/ml |
| --- | --- | --- | --- |
| $8.0 \times 10^4$ | 0.78 | 1.66 | 0.47 |
| $19.5 \times 10^4$ | 0.71 | 1.21 | 0.58 |

EXAMPLE 6

A series of samples were prepared as in Example 1 but the acid concentration was varied. The product silica had the following properties:

| Acid Strength % v/v | Microsphere Size microns | Pore Volume ml/ml | Weight Porosity ml/g | Density g/ml |
| --- | --- | --- | --- | --- |
| 1.75 | 5–8 | 0.78 | 1.91 | 0.41 |
| 2.00 | 3–40 | 0.74 | 1.45 | 0.51 |
| 2.25 | 10–250 | | | |

EXAMPLE 7

10 g starch was dissolved in 100 ml boiling water and then cooled to 18° C. before being added to 50 ml of commercial sodium silicate also at 18° C. To this was added 50 ml 4% v/v sulphuric acid with stirring following by 50 ml 2% w/v sodium alginate solution and the mixture was held at 18° C. for 12 h. The silica microspheres were isolated, washed and dried as in Example 1. The dried material was made up of approximately 5 micron microspheres and had a Pore Volume of 0.83, a Weight Porosity of 3.14 ml/g and a Density of 0.32 g/ml.

EXAMPLE 8

25 g starch was dissolved in 100 ml boiling water which was cooled to 18° C. before being added to 50 ml commercial sodium silicate at 18° C. To this was added 100 ml 2% v/v sulphuric acid with stirring. Stirring was discontinued and the mixture held at 18° C. for 12 h. The silica microspheres formed were approximately 1 micron in diameter.

EXAMPLE 9

The procedure of Example 1 was repeated replacing the sodium alginate solution with a 5% w/v gelatin solution. The microspheres produced were 0.5 to 2.0 microns in diameter.

EXAMPLE 10

The procedure of Example 1 was repeated replacing the sodium alginate solution with a 10% w/v pectin solution. The microspheres produced were approximately 0.5 to 2 microns in diameter. The Pore Volume was 0.62 ml/ml, the Weight Porosity was 0.77 ml/g and the Density was 0.81 g/ml.

EXAMPLE 11

20 ml of 2% sulphuric acid was added with stirring to 20 ml of a 50% solution of commercial sodium silicate followed by 10 ml of 4% sodium alginate. After 4 hours the alginate solution containing the silica was dripped through a 2 mm oriface into a solution of 0.1M calcium nitrate in 1% nitric acid to form gel beads. These were washed, dried and heated to 550° C. to decompose the alginate forming 3 mm diameter porous beads. Electron microscope examination showed that these were made up of 5 to 10 micron microspheres fused at their points of contact and enclosing a well developed pore structure. The Pore Volume was 0.53 ml/ml.

What is claimed is:

1. A method of preparing microparticles of silica consisting of the step adding an acid solution ot a solution of soluble silicate and prior to the formation of a silica gel adding an organic polymer solution, the polymer being selected from the group consisting of an alkali metal alginate, ammonium alginate, starch, gelatin, pectin, or a mixture thereof.

2. A method as claimed in claim 1, wherein the acid solution is added to the soluble silicate before addition of the alkali metal alginate, ammonium alginate, starch, gelatin, pectin or mixtures thereof.

3. A method as claimed in claim 1, wherein the acid solution is added to the soluble silicate after addition of the alkali metal alginate, ammonium alginate, starch, gelatin, pectin or mixtures thereof.

4. A method as claimed in claim 1, wherein the microparticles are substantially spherical.

5. A method as claimed in claim 4, wherein the microparticles have diameters of between 0.5 and 250 microns.

6. A method as claimed in claim 1 wherein the silicate solution contains from 3 to 25% w/v silica.

7. A method as claimed in claim 1 wherein the acid solution contains from 1 to 10% by volume of acid.

8. A method as claimed in claim 1 wherein the pH of the reaction mixture is maintained above 7.

9. A method as claimed in claim 1, wherein the solutions are maintained at a temperature of between 0° C. and 100° C.

10. Microparticles of silica prepared by the method as claimed in claim 1.

* * * * *